United States Patent [19]

Flanagan et al.

[11] Patent Number: 5,556,939
[45] Date of Patent: Sep. 17, 1996

[54] TC OR RE RADIONUCLIDE LABELLED CHELATE, HEXAPEPTIDE COMPLEXES USEFUL FOR DIAGNOSTIC OR THERAPEUTIC APPLICATIONS

[75] Inventors: Richard J. Flanagan, St. Lazare; Jean-Marc Dufour, Pierrefonds; Keith T. Hogan, Dorval, all of Canada

[73] Assignee: Merck Frosst Canada, Inc., Kirkland, Canada

[21] Appl. No.: 322,880

[22] Filed: Oct. 13, 1994

[51] Int. Cl.$^6$ ............ A61K 38/12; A61K 51/08; C07F 13/00; C07K 7/64

[52] U.S. Cl. ............ 530/311; 530/321; 530/345; 534/10; 534/14; 930/160

[58] Field of Search ............ 930/160; 534/10, 534/14; 424/1.69; 514/11, 17; 530/311, 321, 345, 391.5, 391.9, 404

[56] References Cited

U.S. PATENT DOCUMENTS

| | | | |
|---|---|---|---|
| 3,780,015 | 12/1975 | Hirschmann et al. | 530/337 |
| 5,225,180 | 7/1993 | Dean et al. | 530/311 |
| 5,382,654 | 1/1995 | Lyle et al. | 530/311 |

FOREIGN PATENT DOCUMENTS

| | | |
|---|---|---|
| 0150844A2 | 8/1985 | European Pat. Off. |
| 0187622A2 | 7/1986 | European Pat. Off. |
| 0233619A1 | 8/1987 | European Pat. Off. |
| 0247866A1 | 12/1987 | European Pat. Off. |
| 2199831 | 7/1988 | United Kingdom |
| 2206352 | 1/1989 | United Kingdom |
| 2225579 | 6/1990 | United Kingdom |
| 2225579 | 3/1993 | United Kingdom |
| WO87/00181 | 1/1987 | WIPO |
| WO90/06949 | 6/1990 | WIPO |

OTHER PUBLICATIONS

Nucl. Med. Biol., vol. 15, No. 2, issued 1988, Chiotellis et al, "Comparctive Evaluation of $^{99m}$Tc–labeled Aminothiols . . . ", pp. 215–223.

Reubi, J. C., et al., Cancer Research, 47, pp. 5758–5764, Nov. 1, 1987.

Spanevello, R. A., et al., Tetra. Letters, vol. 32, pp. 4675–4678, 1991.

Primary Examiner—Jeffrey E. Russel
Attorney, Agent, or Firm—J. Eric Thies; David L. Rose

[57] ABSTRACT

Technetium or rhenium radionuclide labelled chelate-hexapeptide complexes are useful for the selective detection or treatment of tumors with somatostatin receptors. In particular, compounds of formula:

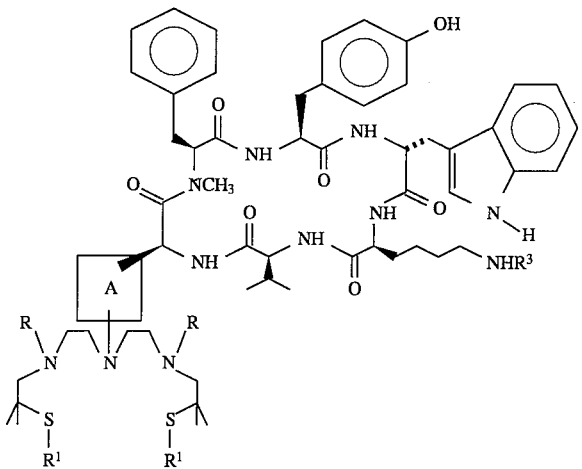

(wherein R, R$^1$, R$^3$ and A are as defined herein) incorporating an N3S2 chelate may be labelled with a radionuclide. The resulting complexes are useful as radioimaging agents or as radiopharmaceuticals for the treatment of certain tumors.

7 Claims, No Drawings

TC OR RE RADIONUCLIDE LABELLED CHELATE, HEXAPEPTIDE COMPLEXES USEFUL FOR DIAGNOSTIC OR THERAPEUTIC APPLICATIONS

BACKGROUND OF THE INVENTION

In the last few years a high incidence of somatostatin receptors has been demonstrated in a variety of human ramors, e.g., pituitary tumors, neuroendocrine tumors, breast tumors, gastro-enteropancreatic tumors and their metastases. Some of them are small or slow-growing tarnors which are difficult to precisely localize by conventional diagnosis methods.

In vitro visualization of somatostain receptors has been performed through autoradiography of tumoral tissues using radioiodinated somatostatin analogues, e.g., [$^{125}$I-Tyr$^{11}$] somatostatin- 14 (Taylor, J. E. et al., *Life Science* (1988) 43:421) or [$^{125}$I-Tyr$^{3}$]SMS 201–995 also called [$^{125}$I] 204–090 (Reubi, J. C. et at., *Brain Res.* (1987) 406:891; Reubi, J. C. et al.,*J. Clin. Endocr. Metab.* (1987) 65:1127; Reubi, J. C. et al., *Cancer Res.* (1987) 47:551; Reubi, J. C. et al., *Cancer Res.* (1987) 47:5758).

Although some somatostatin peptides are useful in therapeutic or in vivo diagnostic applications, not all radioisotypes commonly employed in the medical community have been easy to chelate or label in it.

SUMMARY OF THE INVENTION

According to the invention, synthetic hexapeptides are chelated with a bifunctional ligand bearing at least one chelating group for a detectable element, such as technetium or rhenium and furthermore, the chelation can be done at relatively mild conditions.

The synthetic hexapeptides useful in this invention are those disclosed in Tet. Letters, Vol. 32:36, pp 4675–4678 (1991). The best compound is:

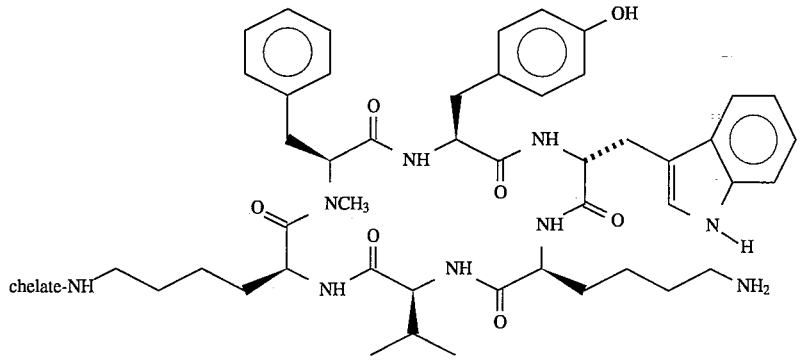

wherein the chelate is as defined herein.

This compound possesses the singular property of being capable of binding to the appropriate binding site and also containing a chelate group capable of attaching radionuclides. Metallic isotopes such as Tc-m99, In-111, Re-186, or Re-188 are substantially better from an imaging point of view compared to the standard halogen isotopes (I-123, I-131, 1I-125) but they are much more difficult to attach to peptides and proteins.

Accordingly, the present invention is directed to compounds of the formula:

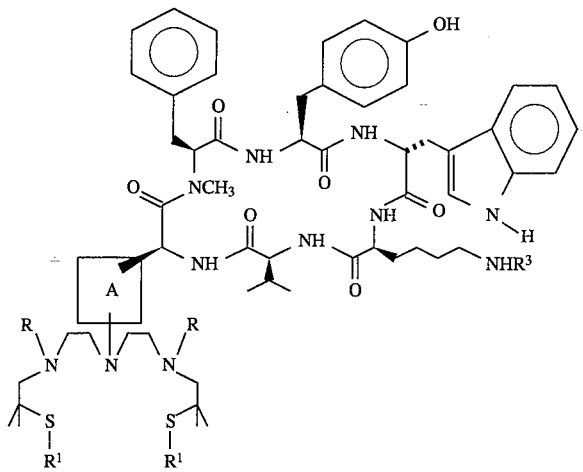

wherein:

R is selected from the group consisting of:
hydrogen,
loweralkyl of 1–4 carbon atoms, and
loweralkyl carboxyl, wherein loweralkyl is 1–4 carbon atoms;

R$^1$ is selected from the group consisting of: hydrogen; a sulfur protecting group, such as p-loweralkyloxyl (1–4 carbon atoms) benzy, p-methoxybenzyl, or trityl; or R$^1$ R$^2$ are linked together to form a bond between the two "S"groups; m and n are independently an integer from 1-14 4; R$^3$ is hydrogen or an easily removable blocking group such as t-butoxycarbonyl (t-boc), fluorentlmethoxycarbonyl (Fmoc), or isonicotinyloxycarbonyl (i-Noc); and the linker

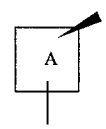

is selected from the group consisting of:

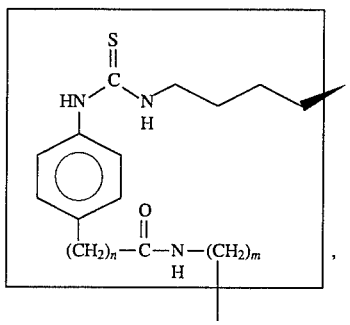

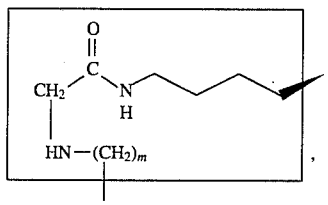

and

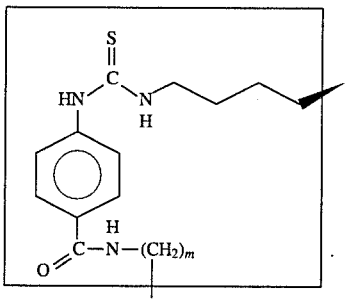

The synthetic hexapeptides can be chelated with a group of N3S2 chelates which are a separate invention, (Attorney Docket 19215, Ser. No. 08/322,881, filed Oct. 13, 1994. This group of N3S2 chelates (or ligands) having the following structure:

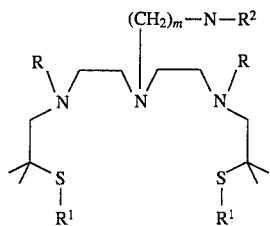

wherein

R is hydrogen, loweralkyl of 1–4 carbon atoms, or loweralkyl carboxyl, wherein loweralkyl is 1–4 carbon atoms;

$R^1$ is hydrogen, a suitable protecting group such as p-loweralkyloxyl (1–4 carbon atoms) benzyl such as p-methoxybenzyl; trityl; or $R^1$ and $R^1$ are linked together to form a bond between the two "S" groups; and $R^2$ is either a free amino or an isothiocyanato group, which can be =C=S or $-H_2$;

-continued

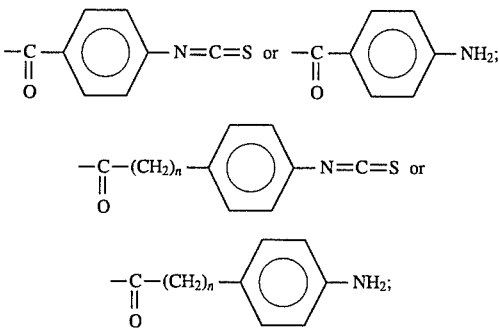

and n or m are independently an integer from 1–4.

These ligands are prepared by using either a cyclic approach, when $R^1$ and $R^1$ are linked together to form the disulfide bond; or an open chain approach when $R^1$ and $R^1$ are either hydrogen or the protecting group.

The cyclic approach reacts a tris(2-aminoethyl)amine with the appropriate dithio-dialdehyde in a suitable solvent such as lower alkanol at reflux. Thereafter, the cyclic amine is optionally reacted on the secondary amine groups, to provide the desired R groups, and subsequently with the appropriate N-hydroxy succinimide ester in triethylamine and dichloromethane to yield compoundsin which $R^2$ is the amino group; and subsequently optionally reacted with thiophosgene to yield the corresponding isothiocyanato derivatives.

The open chain approach utilizes a diethylenetriamine reaction with first phthalic arthydride; second, p-nitrobenzyl bromide; and third, 6N HCl at reflux to yield the appropriate N'-(4-nitrobenzyl)-bis-( 2'-phthalimidoethyl)amine, to which subsequently the pendent blocking groups are attached, followed by reaction of the amino group to isothiocyanato if desired.

The N3S2 ligands can then be labelled with the appropriate radioisotope by reacting in a methanolic solution with the radioisotope as a glucoheptonate reagent (available commercially) and heating at 40°–80° C. for 1–4 hours. Alternatively, the N3S2 ligands can be coupled with the appropriate peptide or protein and then radiolabelled using a similar procedure.

The N3S2 ligands are therefore useful as radioimaging agents after labelling, or as radiopharmaceutical for the treatment of appropriate tumors. When the ligands are to be first coupled with the peptide or protein, the isothiocyanate group at $R^2$ is first prepared for reaction with the amino group of the peptide or protein; and thereafter chelated with the appropriate radiolabelling agent.

As previously mentioned, the ligands are coupled with the desired synthetic hexapeptide, preferably:

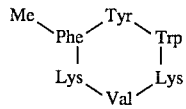

The preferred radioisotope is one of those of rhenium or technetium, preferably Re-186 or Tc-m99, respectively.

Other radioisotopes can be used which can be any detectable element. By detectable element is meant any element, preferably a metal ion which exhibits a property detectable in therapeutic or in vivo diagnostic techniques, e.g., a metal ion which emits a detectable radiation or a metal ion which is capable of influencing NMR relaxation properties.

Suitable detectable metal ions include, for example heavy elements or rare earth ions, e.g., as used in CAT scanning (Computer axial tomography), paramagnetic ions, e.g., $Gd^{3+}$, $Fe^{3+}$, $Mn^{2+}$ and $Cr^{2+}$, fluorescent metal ions, e.g., $Eu^{3+}$, and radionuclides, e.g., γ-emitting radionuclides, β-emitting radionuclides, α-emitting radionuclides, positron-emitting radionuclides, e.g., $^{68}Ga$.

The products of this invention are useful either as an imaging agent, e.g., visualization of the particular (peptide) receptor positive tumors and metastases when complexed with a paramagnetic, a γ-emitting metal ion or a positron-emitting radionuclide, or as a radiopharmaceutical for the treatment in vivo of (peptide) receptor positive tumors and metastases when complexed with a α- or β-radionuclide, as indicated by standard tests.

The particular radioisotope chosen is relevant to the organ or system to be radioimaged. For instance, in the last few years a high incidence of somatostatin receptors has been demonstrated in a variety of human tumors, e.g., pituitary tumors, central nervous system tumors, breast tumors, gastroenteropancreatic tumors and their metastases. Some of them are small or slow-growing tumors which are difficult to precisely localize by conventional diagnosis methods, but in vitro visualization of somatostatin receptors has been performed through autoradiography of tumoral tissues using radioiodinated somatostatin analogues.

The products of this invention when used as imaging agents may be administered parenterally, preferably intravenously, e.g., in the form of injectable solutions or suspensions, preferably in a single injection. The appropriate dosage will of course vary depending upon, for example, the precise chelating ligand and the type of detectable element used, e.g., the radionuclide. A suitable dose to be injected is in the range to enable imaging by photoscanning procedures known in the art. It may advantageously be administered in a dose having a radioactivity of from 0.1 to 50 mCi, preferably 0.1 to 30 mCi, more preferably 0.1 to 20 mCi. An indicated dosage range may be of from 1 to 200 μg product labelled with 0.1 to 50 mCi, preferably 0.1 to 30 mCi, e.g., 3 to 15 mCi, γ-emitting radionuclide, depending on the γ-emitting radionuclide used.

The enrichment in the mmorigenic sites with the products may be followed by the corresponding imaging techniques, e.g., using nuclear medicine imaging instrumentation, for example a scanner, γ-camera, rotating γ-camera, each preferably computer assisted; PET-scanner (Positron emission tomography); MRI equipment or CAT scanning equipment.

These products can also be used for in vivo treatment of peptide receptor positive tumors and metastases in a subject in need of such a treatment which comprises administering to said subject a therapeutically effective amount of the product.

Dosages employed in practicing the therapeutic method of the present invention will of course vary depending, e.g., on the particular condition to be treated, for example the volume of the tumor, the particular product employed, for example the half-life of the product in the tumor, and the therapy desired. In general, the dose is calculated on the basis of radioactivity distribution to each organ and on observed target uptake. For example, the product may be administered at a daily dosage range having a radioactivity of from 0.1 to 3 mCi/kg body weight, e.g., 1 to 3 mCi, preferably 1 to 1.5 mCi/kg body weight. An indicated daily dosage range is of from 1 to 200 μg ligand labelled with 0.1 to 3 mCi/kg body weight, e.g., 0.1 to 1.5/kg body weight αx- or β-emitting radionuclide, conveniently administered in divided doses up to 4 times a day.

These products may be administered by any conventional route, in particular parenterally, e.g., in the form of injectable solutions or suspensions. They may also be administered advantageously by infusion, e.g., an infusion of 30 to 60 min. Depending on the site of the tumor, they may be administered as close as possible to the tumor site, e.g., by means of a catheter. The mode of administration selected may depend on the dissociation rate of the product used and the excretion rate.

These products may be administered in free form or in pharmaceutically acceptable form, such as salts which may be prepared in conventional manner and exhibit the same order of activity as the free compounds.

The products for use in the method of the present invention may preferably be prepared shortly before the administration to a subject, i.e., the radiolabelling with the desired detectable metal ion, particularly the desired α-, β- or γ-radionuclide, may be performed shortly before the administration.

They are then suitable for imaging or treating tumors such as pituitary, gastroenteropancreatic, central nervous system, breast, prostatic, ovarian or colonic tumors, small cell lung cancer, paragangliomas, neuroblastomas, pheochromocytomas, medullary thyroid carcinomas, myelomas, etc. and metastases thereof, as well as lymphomas.

According to a further aspect of the invention, there is provided:

i. a pharmaceutical composition comprising the radiolabelled product of the invention in free or in pharmaceutically acceptable salt form, together with one or more pharmaceutically acceptable carriers or diluents therefor; or ii. a pharmaceutical composition comprising a chelate-peptide product according to the invention in free or in pharmaceutically acceptable salt form, together with one or more pharmaceutically acceptable carriers or diluents therefor.

Such compositions may be manufactured in conventional manner.

A composition according to the invention may also be presented in separate package with instructions for mixing the chelate-peptide product with the metal ion and for the administration of the resulting radiolabelled product. It may also be presented in twin-pack form, that is, as a single package containing separate unit dosages of the ligand and the detectable metal ion with instructions for mixing them and for administration of the product. A diluent or carrier may be present in the unit dosage forms.

EXPERIMENTAL

Materials and methods. Unless otherwise specified, all reactions were carried out in oven-dried flasks at room temperature under an argon atmosphere with magnetic stirring. After extraction, organic solvents were dried over $MgSO_4$, filtered, and removed under-reduced pressure on a rotary evaporator. Reagent grade solvents, starting materials and deuterated solvents were purchased from Aldrich Chemical Co. (Milwaukee,WI) and used without further purification.

$^1H$ NMR spectra were obtained on a Bruker Model AM 500, AM 400, and AM 300. Samples were dissolved in $CDCl_3$, $MeOD_4$, or $DMSO-d_6$ and chemical shifts were reported as ε values with the solvent or tetramethylsilane resonance as the internal standard. The multiplicity is defined by s(singlet), d(doublet), t(triplet), q(quartet), and m(multiplet). The relative peak heights of the resonances are reported as integers following the multiplicity. $^{13}C$ NMR spectra were recorded on a Bruker AM-300 spectrometer at 75.5 MHz and the degree of substitution of each carbon atom was determined by complete decoupling and DEPT composed 135° pulsed sequence experiments. For $^{13}C$ the carbon and proton signals were assigned by heterocorrelation experiments.

Infrared(IR) spectra (solution cells-$CDCl_3$ as solvent) were recorded on a Perkin Elmer 681 infrared spectrophotometer. Melting points were determined on a Thomas Hoover capillary melting point apparatus and are uncorrected. Mass spectra(MS) were recorded either in the CI(methane gas) or FAB mode using Finnigan 4500 single quadrupole mass spectrometer and were run by Oneida Research Services, Inc. (Whitesboro, N.Y.). Flash chromatography was performed essentially as described in the literature[1] using Merck silica gel 60 (230–400 mesh) as stationary phase with the use of the following solvents: methanol(M), methylene chloride(C), ammonium hydroxide(H).

Part 1: Cyclic Approaches to $N_3S_2$ Chelates

Synthesis of $N_3S_2$-isothiocyanate (11) TPPBI 3,3,13,13-Tetramethyl- 1,2-dithia-5,8,11-triazacyclotridecan-8-yl-ethanamine (4)

A round bottom flask was charged with tris(2-aminoethyl)-amine (1) (989 mg, 6.76 mmol), α,α'-dithiodiiso-butyraldehyde (2) (1,380 mg, 6.69 mmol prepared according to reference 2b) and ethanol (200 ml). The mixture was stirred at room temperature for 1.5 hours and then refluxed for 3 hours. After cooling the volatile materials were removed in vacuo to give the crude di-imine 3 as a glassy solid. $^1H$ NMR analysis of the di-imine 3 gave three singlets centered at 7.58 ppm (17:67:17) confirming the formation of an imine.

To the crude di-imine 3 in refluxing ethanol (200 mL) was added sodium borohydride (1.346 g, 35.58 mmol) in two portions over 3.5 hours. The reaction mixture was refluxed for a total of 17 hours and acetone (100 ml) was added to destroy excess reagent. After cooling the solvent was removed in vacuo, water was added, and the product was extracted with 5% $MeOH/CH_2CL_2$. The organic layer was dried ($MgSO_4$), filtered, and concentrated in vacuo to give a yellow oil. Flash chromatography of this oil using 82.5% C/15.0% M/2.5% H gave amine 4 as a light yellow viscous oil (1.268 g, 59.5% yield). $^1H$ NMR (in $CDCl_3$): δ2.83 (t,j=5.9 Hz,2H,N—$CH_2CH_2$—$NH_2$), 2.72 (s,4H,2N—$CH_2$—C—S), 2.70 (m,4H,2N—$CH_2CH_2$—NH), 2.58 (m,4H,2N—$CH_2$—$CH_2$—NH), 2.50 (t,j=5.9 Hz,2H,N—$CH_2CH_2$—$NH_2$), 1.73 (br s,4H,4NH), 1.33 (s,12H,4$CH_3$—C—S) ppm. $^{13}C$ NMR (in $CDCl_3$): 59.2 (t,2NH—$CH_2$—C—S), 56.6 (t,N—$CH_2CH_2$—$NH_2$), 54.5 (t,2N—$CH_2CH_2$—NH), 50.5 (s,2$CH_3$—C—S), 47.4 (t,2N—$CH_2CH_2$—NH), 39.6 (t,N—$CH_2CH_2$—$NH_2$), 27.4 (q,4$CH_3$—C—S) ppm. MS (m/z,CI): 321(100, $M^+$+1). IR ($CDCl_3$): 3350, 2940, 2820, 1455, 1360, 1120 $cm^{-1}$.

3,3,13,13-Tetramethyl- 1,2-dithia-5,8,11-triazacyclotridecan-8-yl-(2'-N-phthaloyl)-ethanamine (5)

A round bottom flask was charged with amine 4 (111.2 mg, 0.347 mmol), N-carboethoxyphthalimide (108.3 mg, 0.494 mmol), and dichloromethane (10 mL). The reaction mixture was stirred at room temperature for 1 hour and the solvent was removed in vacuo. Flash chromatography of the residue using 90% C/9.5% M/0.5% H gave the phthalate 5 as a yellowish oil (119.2 mg, 76.3%). $^1H$ NMR (in $CDCl_3$): δ7.86 (m,2H,$H_2$&$H_5$—Ar), 7.71 (m,2H,$H_3$&$H_4$—Ar), 3.84 (t,j=6.4 Hz,2H,N—$CH_2CH_2$—NPhth), 2.81 (t,j=6.4 Hz,2H, N—$CH_2CH_2$—NPhth), 2.69 (m,4H,2N—$CH_2CH_2$—NH), 2.66 (m,4H,2N—$CH_2CH_2$—NH), 2.59 (s,4H,2N—$CH_2$—C—S), 1.87 (br m,2H,2NH), 1.23 (s,12H,4$CH_3$—C—S) ppm. $^{13}C$ NMR (in $CDCl_3$): 168.1 (s,2CO), 133.7 (d,$C_3$&$C_4$-Ar), 131.9 (s,$C_1$&$C_6$—Ar), 123.3 (d,$C_2$&$C_5$—Ar), 58.7 (t,2NH—$CH_2$—C—S), 53.9 (t,2N—$CH_2CH_2$—NH), 52.8 (t,N—$CH_2CH_2$—NPhTh), 50.2 (s,2$CH_3$—C—S), 47.6 (t,2N—$CH_2CH_2$—NH), 35.8 (t,N-$CH_2CH_2$—NPhTh), 27.3 (q,4$CH_3$—C—S) ppm. MS (m/z,CI): 451(100, $M^+$+1). IR ($CDCl_3$): 3400, 2950, 2810, 1770, 1705, 1465, 1395 $cm^{-1}$.

3,3,5,11,13,13-Hexamethyl- 1,2-dithia-5,8,11-triazacyclotridecan-8-yl-ethanamine (7)

A round bottom flask was charged with phthalate 5 (775.7 mg, 1.72 mmol), formic acid (10 mL, 265 mmol), and formaldehyde (37% wt in water, 15 mL, 200 mmol). The reaction mixture was refluxed for 20 hours and then allowed to cool and the solvent was removed in vacuo. A solution of 10% KOH was added to the solid residue and the compound extracted with 5% $MeOH/CH_2CL_2$. The organic solvent was dried ($MgSO_4$), filtered, and concentrated in vacuo to give crude 6 as a viscous oil.

To a round bottom flask was added crude 6, hydrazine monohydrate (1 mL, 20.6 mmol), and ethanol (40 mL). The reaction mixture was refluxed for 20 hours and then allowed to cool. The solvent was removed in vacuo, water added, and the residue extracted with 5% $MeOH/CH_2Cl_2$. The organic solvent was dried ($MgSO_4$), filtered, and concentrated in vacuo to give a yellowish viscous oil. Flash chromatography of the crude product using 80% C/19.5% M/1.0% H gave dimethyltetramine 7 as a light yellow oil (375 mg, 62.4% overall yield from 4). $^1H$ NMR (in $CDCl_3$): δ2.78 (t,j=5.9 Hz,2H,N—$CH_2CH_2$—$NH_2$), 2.72 (t,j=5.5 Hz,4H,2N—$CH_2CH_2$—$NCH_3$), 2.63 (s,4H,2N—$CH_2$—C—S), 2.60 (t,j=5.5 Hz,4H,2N—$CH_2CH_2$—$NCH_3$), 2.42 (t,j=5.9 Hz,2H, N—$CH_2CH_2$ -$NH_2$), 2.36 (s,6H,2$NCH_3$), 1.77 (br s,2H, $NH_2$), 1.28 (s,12H,4$CH_3$—C—S) ppm. $^{13}C$ NMR (in $CDCl_3$): 67.2 (t,2N—$CH_2$—C—S), 57.9 (t,2N—$CH_2$ $CH_2$—$NCH_3$), 55.6 (t,N—$CH_2CH_2$—$NH_2$), 52.1 (t,2N—$CH_2CH_2$—$NCH_3$), 51.3 (s,2$CH_3$—C—S) 45.1 (q,2$NCH_3$), 39.5 (t,N—$CH_2CH_2$—$NH_2$), 27.4 (q,4$CH_3$—C—S) ppm. MS (m/z,CI): 349(100,$M^+$+1). IR ($CDCl_3$): 2960, 2800, 1455, 1355, 1310, 1100 $cm^{-1}$.

4-Amino-N-[ 2-(3,3,5,11,13,13-hexamethyl- 1,2-dithia-5, 8,11-triazacyclo-tridecan-8-yl)ethyl]benzamide (10)

A round bottom flask was charged with the dimethyltetramine 7 (514.9 mg, 1.48 mmol), tBoc-p-aminobenzoyl N-hydroxysuccinimide ester (8) (493.8 mg, 1.48 mmol, prepared according to reference 3), triethylamine (0.21 mL, 1.51 mmol), and dichloromethane (40 mL). The reaction mixture was stirred at room temperature for 12 hours and the solvent was removed in vacuo to give crude 9.

To a round bottom flask was added crude 9, dichloromethane (10 mL), and trifluoroacetic acid (10 mL) and the resulting mixture was stirred at room temperature for 1 hour. The solvent was removed in vacuo and purification by flash chromatography of the residue using 94.5% C/5.0% M/0.5%

H gave the aniline 10 as a yellowish white solid (345.8 mg, 50.8% overall yield from dimethyltetramine 7). $^1$H NMR (in CDCl$_3$): δ7.65 (d,j=8.6 Hz,2H,H$_2$&H$_6$—Ar), 6.87 (br s,1H, NH—CO), 6.67 (d,j=8.6 Hz,2H,H$_3$&H$_5$—Ar), 3.95 (s,2H, NH$_2$), 3.49 (t,j=5.4 Hz,2H,N—CH$_2$CH$_2$—NCO), 2.74 (m,4H,2N—CH$_2$CH$_2$—NCH$_3$), 2.65 (m,4H,2N—CH$_2$CH$_2$—NCH$_3$), 2.61 (s,4H,2N—CH$_2$—C—S), 2.53 (t,j= 5.4 Hz,2H,N—CH$_2$CH$_2$—NCO), 2.30 (s,6H,2NCH$_3$), 1.29 (s,12H,4CH$_3$—C—S) ppm. $^{13}$C NMR (in CDCl$_3$): 167.1 (s,NHCO), 149.6 (s,C$_1$—Ar), 128.6 (d,C$_3$&C$_5$—Ar), 123.9 (s,C$_4$—Ar), 113.9 (d,C$_2$&C$_6$-Ar), 67.2 (t,N—CH$_2$—C—S), 57.6 (t,2N—CH$_2$CH$_2$—NCH$_3$), 53.7 (t,N-CH$_2$ CH$_2$—NHCO), 53.4 (s,2CH$_3$—C—S), 51.4 (t,2N—CH$_2$CH$_2$—NCH$_3$), 53.7 (t,N-Ch (q,2NCH$_3$), 37.0 (t,N—CH$_2$CH$_2$—NHCO), 27.2 (q,4CH$_3$—C—S) ppm. MS (m/z,FAB): 468.2( 100, M$^+$+1). IR (CDCl$_3$): 3405, 2960, 2800, 1620, 1495, 1280, 1100, 835 cm$^{-1}$.

4-Isothiocyanato-N-[2-(3,3,5,11,13,13-hexamethyl-1,2-dithia-5,8,11-triazacyclotridecan- 8-yl)ethyl]benzamide (11) [TPPBI]

To a round bottom flask with the aniline 10 (53.3 mg, 0.114 mmol) and dichloromethane (5 mL) was added 0.2007M solution of thiophosgene (0.60 mL, 0.120 mmol) in dichloromethane. The heterogeneous reaction mixture was stirred at room temperature for 1 hour and the solvent was removed in vacuo to give the isothiocyanate 11 as a reddish solid (67.8 mg, 116%). $^1$H NMR (in DMSO-d$_6$): δ8.88 (br s,1H,NH—CO), 7.99 (d,j=8.4 Hz,2H,H$_2$&H$_6$—Ar), 7.54 (d,j=8.4 Hz,2H,H$_3$&H$_5$—Ar), 3.49 (m,2H,N—CH$_2$CH$_2$—NCO), 3.40 (m,8H,2N—CH$_2$CH$_2$—NCH$_3$), 3.01 (s,4H,2N—CH$_2$—S), 2.89 (s,6H,2NCH$_3$), 2.71 (m,2H$_2$q—CH$_2$CH$_2$—NCO), 1.45 (s,12H,4CH$_3$—C—S) ppm. MS (m/z,CI): 510(100, M$^+$+1). IR (CDCl$_3$): 3400, 2960, 2100, 1640, 1600, 1545, 1500, 1470, 1300 cm$^{-1}$.

Preparation of Somatoscan(Fmoc)TPPBI (13)

In a 5 mL Reacti-Vial (Pierce) a solution of Somatoscan-Fmoc (12) [cyclo(Trp-Lys(Fmoc)-Val-Lys-NMe-Phe-Tyr)] (1.97 mg; 1.515 umol), TPPBI (11) (8.4 mg, 16.495 umol), and DMF (400 µL) was stirred while bicarbonate/phosphate buffer (0.2M, pH 8.2, 100 µL, freshly prepared) was added. The heterogeneous solution was monitored by HPLC and stirred for 4 hours at room temperature. The solvents were removed in vacuo and the residue was partitioned with 1N HCl (300 µL) and MeOH (100 µL). Purification of this solution by HPLC (Hamilton PRP-1 12–20 µm preparative column 250×21.5 mm) using a 30% to 100% gradient of acetonitrile: water (containing 0.1% TFA) over 40 minutes (flow rate of 12 ml/min) afforded pure Somatoscan(Fmoc)-TPPBI (13) (R$_t$=20.64 min).

MS (Electrospray, Hypennass) 799.4(z=2), Calc. Compound Mass=1596.8, Meas. Compound Mass=1597.8.

Part 2: Acyclic Approaches to N$_3$S$_2$ Chelates

Synthesis of Acyclic Dimercaptoanisidine ArylisothioCyanates

Synthesis of Open chain N$_3$S$_2$-aryl isothiocyanate (21)

Bis(2'-phthalimidoethyl)amine, (15)

This was prepared according to reference 4.

Phthalic anhydride (32 g; 0.22 mol) was dissolved in 333 mL of hot chloroform and the mixture was filtered to eliminate phthalic acid*. A Diethylenetriamine 14 (7.97 g; 0.077 mol) solution in chloroform (64 mL) was slowly added (over a period of 50 minutes) to the phthalic anhydride mixture maintained at a temperature of 50° C. Temperature was raised to 110° C. after the addition was over. The reaction mixture was then stirred for 48 hours and slowly concentrated. The concentrate solution was then treated with activated charcoal. 31.8 g of a yellow solid was recovered after evaporation of the solvent under reduced pressure. The solid was triturated successively with ether, ethanol and then dissolved in methylene chloride. The methylene chloride solution was washed with 10% sodium carbonate (3×500 mL), water and saturated sodium chloride solution. The organic phase was dried with magnesium sulfate, filtered and evaporated to dryness under reduced pressure. A pale yellow solid (14.47 g; 52%) was obtained. A portion (4.45 g) of that product was purified by flash chromatography (silica gel) using a mixture of methylene chloride, ethyl acetate and triethylamine as elution system (79/20/1). The purification give 2.798 g of bis(phthalimidoethyl)amine (15). * 6.96 g of phthalic acid was recovered. $^1$H NMR (in CDCl$_3$): δ7.70 (m,8H,H-Ar(phth)), 3.77 (t,J=6 Hz,4H, —NH(—CH$_2$—CH$_2$—NPhth)$_2$), 2.95 (t,J=6 Hz,4H, —NH(—CH$_2$—CH$_2$—NPhth)$_2$), 1.41 (broad,1H,—NH(—CH$_2$—CH$_2$—NPhth)$_2$) ppm. IR (in CDCl$_3$/NaCl): 3460 (N-H,w, sec amine), 2940–2820 (C–H), 1770–1710 (C=O, Phth), 1465, 1425, 1390, 1360, 1185, 1035 cm$^{-1}$. MS (EI; m/z): 363(0.4,M$^+$), 364(4,M$^+$+1), 216(3 ,M$^+$—Phth), 204(18), 203(100,M$^+$—(Phth—CH$_2$•)), 174(57,Phth—CH$_2$—CH$_2$$^+$), 160(5), 147(6), 130(12)and 56(6).

N'-(4-Nitrobenzyl) bis(2'-phthalimidoethyl)amine (16)

(See Ref. 4) In a 250 mL round bottom flask potassium hydroxyde (1.6 g; 28 mmol) was dissolved in hot ethanol (100 mL). To that ethanolic solution Bis(2'-phthalimidoethyl)amine (15) (10.02 g; 28 mmol) was added. The solution was magnetically stirred and refluxed for 2½ hours before p-nitrobenzyl bromide (5.95 g; 28 mmol; 1 eq) was added. The reaction mixture was heated at reflux for 16 additional hours then filtered hot. The solid obtained previously was washed with absolute ethanol and dried under vacuum to yield 7.441 g (54%) of a white solid (p-nitrobenzyl bisphthalimide). The tiltrate was evaporated under reduced pressure to give 8.19 g of a yellow solid. That residue was purified by flash chromatography (silica gel: 400 g) using methylene chloride-methanol (98/2) system as eluent. The purification by chromatography produced 3.13 g (23%) of the desired product. The alkylation reaction yielded 10.571 g of N'-(4-nitrobenzyl) bis(2'-phthalimidoethyl)amine. (16) $^1$H NMR (in CDCl$_3$): δ7.70 (m,10H,H—Ar(Phth)+o(H)—Ar—NO$_2$), 7.20 (d, J=9 Hz,2H, m(H)—Ar—NO$_2$), 3.75 (t, J=6 Hz, 4H,—NH (—CH$_2$—CH$_2$—NPhth)$_2$), 3.71 (s, 2H,—N—CH$_2$—Ar—NO$_2$) and 2.80 (t, J=6 Hz,4H,—NH(—CH$_2$—CH$_2$—NPhth)$_2$) ppm. MS (EI; m/z): 498(1,M$^+$), 499(0.6,M$^+$+1), 362(1 ,M$^+$—•CH$_2$Ar—NO$_2$), 339 (32, M$^+$+1—(Phth-CH$_2$•)), 338 (100, M$^+$—(Phth—CH$_2$•)), 324 (2, M$^+$—(Phth—CH$_2$—CH$_2$•)), 174(58,Phth—CH$_2$—CH$_2$$^+$), 173(42), 165(6), 163(8), 161(6), 160(43), 149(12), 136(24), 130(12), 106(21), 105(12), 104(17), 90(22), 89(18), 78(23), 77(21) and 76(12).

Hydrolysis of N'-(4-nitrobenzyl) bis(2'-phthalimidoethyl)amine

In a 250 mL round bottom flask, provided with a condenser, N'-(4-nitrobenzyl) bis(2'-phthalimidoethyl)amine (16) (2.80 g; 5.62 mmol) and 6N hydrochloric acid (150 mL) were introduced. The reaction mixture was stirred and refluxed for 23 hours. The solution was cooled with an ice bath and filtered. The filtrate was washed with ether (3×100 mL) and dried by vacuum to give a yellow foam-like material (2.17 g). The residue was dissolved in water (10 mL) and the pH of that solution was brought basic with 1N sodium hydroxide (25 mL). Then the mixture was extracted with methylene chloride (3×75 mL). The organic extracts were combined, dried with magnesium sulfate, filtered and evaporated to dryness to yield 1,347 g of N'-(4-nitrobenzyl) bis(2'-aminoethyl)amine (17) as a light orange oil (which turn dark red with time).

Note: The p-nitrobenzyltriamine (17) is stored for short term away from light and in an inert atmosphere of argon. For long term storage it is better to keep that compound as the hydrochlorate form.

$^1$H-NMR (in CDCl$_3$): $\delta$8.13 (d,J=9 Hz,2H,o(H)—Ar—NO$_2$), 7.46 (d, J=9 Hz, 2H,m(H)—Ar—NO$_2$), 3.65 (s,2H, —N—CH$_2$—Ar—NO$_2$), 2.74 (t,J=6 Hz, 4H, —N(—CH$_2$—CH$_2$—NH$_2$)$_2$), 2.50 (t J=6 Hz,4H,—N(—CH$_2$—CH$_2$—NH$_2$)$_2$) and 1.43 (broad s, 4H,—N(—CH$_2$—CH$_2$—NH$_2$)$_2$) ppm. IR (film): 3370–3290 (N—H,—NH$_2$), 2940–2800(C–H), 1605 (C=C,Ar), 1510 (N=O,Ar), 1450, 1340 (N=O,Ar), 1105, 1010, 850 (C—N,Ar—NO$_2$) and 730 cm$^{-1}$. N'-4-Aminobenzyl-diethylenetriamine (18)

This was prepared according to reference 4. $^1$H NMR (in CDCl$_3$): $\delta$7.08 (d,j=8.3 Hz,2H,H$_3$&H$_5$—Ar), 6.64 (d,j=8.3 Hz,2H,H$_2$&H$_6$—Ar), 3.62 (br s,2H,Ar-NH$_2$), 3.48 (s,2H, N—CH$_2$—Ar), 2.74 (t,j=6.0 Hz,4H,2N—CH$_2$CH$_2$—NH$_2$), 2.50 (t,j=6.0 Hz,4H—2N—CH$_2$CH$_2$—NH$_2$), 1.52 (br s,4H, 2NH$_2$) ppm. N,N"-Bis[2-((4-methoxybenzyl)thio)-2-methyl-propionyl]-N'-(4-aminobenzyl)-diethylenetriamine (20)

To a solution of the aniline 18 (230 mg, 1.10 mmol, freshly prepared) in ethanol (20 mL) was added a solution of 2-[(p-methoxy-benzyl)thio]- 2-methylpropionic acid chloride 19 (1.33 g, 5.10 mmol, prepared according to reference 5) in dichloromethane (10 mL) over 15 minutes. The resulting solution was stirred for 48 hours and the solvent was removed in vacuo, 1 N NaOH was added, and the product was extracted with CH$_2$Cl$_2$. The organic layer was washed with water, dried (MgSO$_4$), filtered, and concentrated in vacuo to give a red oil. Flash chromatography of this oil using 5% MeOH/CH$_2$Cl$_2$ gave the aniline 20 as a yellow oil (126. mg, 17.5% yield). $^1$H NMR (in CDCl$_3$): $\delta$7.15 (d,j=8.6 Hz,4H,2H$_3$&H$_5$—Ar—OCH$_3$), 7.07 (t,j=8.2 Hz,2H, H$_3$&H$_5$—Ar—NH$_2$), 7.07 (m,2H,2NHCO), 6.78 (d,j=8.6 Hz,4H,2H$_2$&H$_6$—Ar—OCH$_3$), 6.58 (d,j=8.2 Hz,2H, H$_2$&H$_6$—Ar—NH$_2$), 3.74 (s,6H,2CH$_3$O), 3.72 (br s,2H, NH$_2$), 3.65 (s,4H,2S—CH$_2$—Ar), 3.49 (s,2H,N—CH$_2$—Ar), 3.24 (q,j=5.9 Hz,4H,2N—CH$_2$CH$_2$—NHCO), 2.55 (t,j=6.2 Hz,4H,2N—CH$_2$CH$_2$—NHCO), 1.50 (s,12H, 4CH$_3$—C—S) ppm. $^{13}$C NMR (in CDCl$_3$): $\partial$174.6 (s,2NCO), 158.9 (s,2C$_1$—Ar—OCH$_3$), 146.0 (s,C$_1$—Ar—NH$_2$), 130.2 (d,C$_3$&C$_5$—Ar—NH$_2$+2C$_3$&C$_5$—Ar—OCH$_3$), 129.6 (s,2C$_1$ &C$_4$—Ar—OCH$_3$), 129.1 (s,C$_4$—Ar—NH$_2$), 115.4 (d,C$_2$&C$_6$—Ar—NH$_2$), 114.3 (d,2C$_2$&C$_6$—Ar—OCH$_3$), 58.3 (t,N—CH$_2$—Ar), 55.5 (q,2CH$_3$O), 53.0 (t,2N—CH$_2$CH$_2$—NHCO), 50.3 (s,2S—C—CH$_3$), 37.8 (t,2N—CH$_2$CH$_2$—NHCO), 34.4 (t,2S—CH$_2$—Ar), 27.1 (q,4CH$_3$—C—S) ppm. MS (m/z,FAB): 653.5(100, MH+). IR (CDCl$_3$): 3380, 3000, 2930, 2835, 1665, 1510, 1245, 1195, 1175, 1035 cm$^{-1}$. N,N"-Bis[2-((4-methoxybenzyl)thio)-2-methyl-propionyl]-N'-(4-isothiocyanatobenzyl)-diethylenetriamine (21)

To a round bottom flask with the aniline 20 (55.7 mg, 0.0853 mmol) and dichloromethane (5 mL) was added 0,2011 M solution of thiophosgene (0.42 mL, 0.0845 mmol) in dichloromethane. The heterogeneous reaction mixture was stirred at room temperature for 1 hour and the solvent was removed in vacuo to give the isothiocyanate 21 as a brown solid (68.9 mg, 116%). $^1$H NMR (in CDCl$_3$): $\delta$7.72 (m,2H,2NHCO), 7.65 (d,j=8.3 Hz,2H,H$_2$&H$_6$—Ar—NCS), 7.25 (t,j=8.3 Hz,2H,H$_3$&H$_5$—Ar—NCS), 7.17 (d,j=8.5 Hz,4H,2H$_3$&H$_5$—Ar—OCH$_3$), 6.80 (d,j=8.5 Hz,4H, 2H$_2$&H$_6$—Ar—OCH$_3$), 4.14 (s,2H,N—CH$_2$—Ar), 3.77 (s,6H,2CH$_3$O), 3.70 (s,4H,2S-CH$_2$—Ar), 3.58 (m,4H,2N—CH$_2$CH$_2$—NHCO), 3.01 (m,4H,2N—CH$_2$CH$_2$-NHCO ), 1.53 (s,12H,4CH$_3$—C—S)ppm. IR (CDCl$_3$): 3300, 2930, 2080, 1655, 1605, 1510, 1245, 1170, 1030 cm$^{-1}$.

Part 3: Synthesis of acyclic dimercaptoanisidine alkyl isothiocyanates

Synthesis of open chain N$_3$S$_2$-alkylanisidine 26

N,N-Bis(2-aminoethyl)-N'-tert-butyl-oxycarbonyl-1,2-ethanediamine (22)

A solution of tris(2-aminoethyl)amine (1) (19.5 g, 133.6 mmol) in CH$_2$Cl$_2$ (300 mL) was cooled to −78° C. in a dry ice-acetone bath while di-tert-butyl dicarbonate (14.6 g, 66.9 mmol) in CH$_2$Cl$_2$ (100 mL) was added slowly over 30 minutes. The reaction mixture was slowly allowed to warm up to room temperature and stirred for 18 hours. 1 N NaOH was added and the organic phase was dried (MgSO$_4$), filtered, and concentrated in vacuo to give the amine 22 as a light yellow oil (9.07 g, 55%). $^1$H NMR (in CDCl$_3$): $\delta$5.62 (br m, 1H,NH—CO), 3.18 (m,2H,N—CH$_2$CH$_2$—NCO), 2.98 (m,4H,2N—CH$_2$CH$_2$—NH$_2$), 2.80 (m,4H,2N—CH$_2$CH$_2$—NH$_2$), 2.57 (m,2H,N—CH$_2$CH$_2$—NHCO), 2.57 (m,4H,2NH$_2$), 1.44 (s,9H,3CH$_3$—C—O) ppm. MS (m/z, CI): 247 (100, MH$^+$). IR (CDCl$_3$): 3280, 2965, 2815, 1695, 1500, 1165, 905,730 cm$^{-1}$. N,N"-Bis[2-((4-methoxybenzyl)thio)-2-methyl-propionyl]-N'-[2-(N-tert-butoxycarbonyl)aminoethyl]-diethylenetriamine (23)

A solution of the 'Boc derivative 22 (555.3 mg, 2.25 mmol) in CH$_2$Cl$_2$ (25 mL) was cooled to 0° C. while 2-[(p-methoxy-benzyl)thio]-2-methylpropionic acid chloride 19 (1.54 g, 6.85 mmol, prepared according to reference 5) in dichloromethane (10 mL) was added over 5 minutes. The resulting solution was allowed to warm to room temperature and stirred for 12 hours. The solvent was removed in vacuo, 1 N NaOH was added, and the product was extracted with CH$_2$Cl$_2$. The organic layer was washed with water, dried (MgSO$_4$), filtered, and concentrated in vacuo to give a yellow oil. Flash chromatography of this oil using 5% MeOH/CH$_2$Cl$_2$ gave the 'Boc derivative 23 as a yellow oil (938 mg, 60.2% yield). $^1$H NMR (in CDCl$_3$): $\delta$7.16 (d,j=8.5 Hz,4H,2H$_3$&H$_5$—Ar—OCH$_3$), 7.07 (t,j=5.2 Hz,2H,2NH—CO), 6.81 (d,—j=8.5 Hz,4H,2H$_2$&H$_6$—Ar—OCH$_3$), 4.98 (br s,1H,NH—CO), 3.77 (s,6H,2CH$_3$O), 3.63 (s,4H,2S—CH$_2$—Ar), 3.17 (m,6H,3N—CH$_2$CH$_2$—NHCO), 2.56

(m,6H,3N—CH$_2$CH$_2$—NHCO), 1.53 (s,12H,4CH$_3$—C—S), 1.42 (s,9H,3CH$_3$—C—O) ppm. MS (m/z,CI): 691 (9, MH$^+$). IR (CDCl$_3$): 3380, 2970, 2930, 2830, 1700, 1650, 1500, 1245, 1170, 1030, 830 cm$^{-1}$.

N,N''-Bis[2-((4-methoxybenzyl)thio)-2-methyl-propionyl]-N'-(2-aminoethyl )-diethylenetriamine (24)

A solution of 23 (858.3 mg, 1.24 mmol) in 50% TFA in CH$_2$Cl$_2$ (30 mL) was stirred at room temperature for 1 hour. The solvent was removed in vacuo, 1 N NaOH was added, and the product was extracted with CH$_2$Cl$_2$. The organic layer was washed with water, dried (MgSO$_4$), filtered, and concentrated in vacuo to give a yellow oil. Flash chromatography of this oil using 90.5% C/9.5% M/0.5% H gave the amine 24 as a yellow oil (734 mg, 95.1% yield). $^1$H NMR (in CDCl$_3$): δ7.25 (m,2H,2NH—CO), 7.16 (d,j=8.5 Hz,4H, 2H$_3$&H$_5$—Ar—OCH$_3$), 6.81 (d,j=8.5 Hz,4H,2H$_2$&H$_6$—Ar—OCH$_3$), 3.77 (s,6H,2CH$_3$O), 3.69 (s,4H,2S—CH$_2$—Ar), 3.23 (q,j=6.1 Hz,4H,2N-CH $_2$CH$_2$—NHCO), 2.72 (t,j=5.9 Hz,2H,N—CH$_2$CH$_2$—NH$_2$), 2.54 (m,6H,N-CH $_2$CH$_2$—NH$_2$+ 2N—CH$_2$CH$_2$—NH—CO), 1.60 (br s,2H,NH$_2$), 1.52 (s,12H,4CH$_3$—C—S) ppm. $^{13}$NMR (in CDCl$_3$): δ174.3 (s,2NH—CO), 158.3 (s,2C$_1$—Ar—OCH$_3$), 129.6 (d,2C$_2$&C$_6$—Ar—OCH$_3$), 128.9 (s,2C$_4$-Ar —OCH$_3$), 113.6 (d,2C$_3$&C$_5$—Ar—OCH$_3$), 54.8 (q,2CH$_3$O), 54.2 (t,N-CH $_2$CH$_2$—NH$_2$), 53.6 (t,2N—CH$_2$CH$_2$—NHCO), 49.4 (s,2S—C—CH$_3$), 38.5 (t,2N—CH$_2$CH$_2$—NHCO), 37.6 (t,N—CH$_2$CH$_2$—NH$_2$), 33.6 (t,2S—CH$_2$—Ar), 26.4 (q,4CH$_3$—C—S) ppm. MS (m/z,CI): 591(31, MH$^+$). IR (CDCl$_3$): 3770, 2930, 2830, 1655, 1510, 1245, 1170, 1030, 830 cm$^{-1}$.

N,N''-Bis[2-((4-methoxybenzyl)thio)-2-methyl-propionyl]-N'-(2-isothiocyanoethyl)-diethylenetriamine (25)

To a round bottom flask containing the aniline 24 (28.8 mg, 0.0487 mmol) and dichloromethane (10 mL) was added 0.2211 M solution of thiophosgene (0.22 mL, 0.0509 mmol) in dichloromethane. The heterogeneous reaction mixture was stirred at room temperature for 1 hour and the solvent was removed in vacuo. Flash chromatography of this crude product using 100% EtOAc gave the isothiocyanate 25 as a clear oil (18.9 mg, 61.3% yield). $^1$H NMR (in CDCl$_3$): δ7.17 (d,j=8.5 Hz,4H,2H$_3$&H$_5$—Ar—OCH$_3$), 7.07 (m,2H,2NH—CO), 6.82 (d,j=8.5 Hz,4H,2H$_2$&H$_6$—Ar—OCH$_3$), 3.78 (s,6H, 2CH$_3$O), 3.70 (s,4H,2S—CH$_2$—Ar), 3.49 (t,j=5.9 Hz,2H,N—CH$_2$CH$_2$-NCS ), 3.21 (q,j=6.2 Hz,4H,2N—CH$_2$CH$_2$—NHCO), 2.78 (t,j=5.9 Hz,2H,N—CH$_2$CH$_2$—NCS), 2.58 (t,j=6.4 Hz,4H, 2N—CH$_2$CH$_2$—NHCO), 1.54 (s,12H,4CH$_3$—C—S) ppm. MS (m/z,CI): 633(25, MH$^+$). IR (CDCl$_3$): 3370, 2950, 2920, 2850, 2100, 1720, 1655, 1610, 1510, 1245, 1170, 1030, 830 cm$^{-1}$.

N,N''-Bis[2-((4-methoxybenzyl)thio)-2-methyl-propionyl]-N'-(2-[[[4-methoxyphenyl )amino]thioxomethyl]aminoethyl]-diethylenetriamine (26)

A solution of the isothiocyanate 25 (18.9 mg, 0.02986 mmol), triethylamine (7.26 mg, 0.07175 mmol), anisidine (6.9 mg, 0.05602 mmol), and CHCl$_3$ (15 mL) was refluxed for 3 hours and the solvent was removed in vacuo. Flash chromatography of this crude product using 100% EtOAc gave the anisidine derivative 26 as a clear oil (19.8 mg, 87.6% yield). $^1$H NMR (in CDCl$_3$): δ8.17 (brs,1H,NH—CS—NH—Ar), 7.28 (d,j=8.8 Hz,2H,H$_2$&H$_6$—Ar—N), 7.15 (d,j=8.6 Hz,4H,2H$_3$&H$_5$—Ar—OCH$_3$), 7.06 (brs,1H, NH—CS—NH—Ar), 7.06 (t,j=5.7 Hz,2H,2NH—CO), 6.90 (d,j=8.9 Hz,2H,H$_3$&H$_5$—Ar—N), 6.82 (d,j=8.6 Hz,4H, 2H$_2$&H$_6$—Ar—OCH$_3$), 3.79 (s,3H,CH$_3$O—Ar—N), 3.77 (s,6H,2CH$_3$O—Ar—CH$_2$), 3.67 (s,4H,2S—CH$_2$-Ar), 3.61 (q,j=5.3 Hz,2H,N—CH$_2$CH$_2$—NHCS), 3.14 (q,j=6.2 Hz,4H,2N-CH $_2$CH$_2$—NHCO), 2.69 (t,j=5.6 Hz,2H,N—CH$_2$CH$_2$—NHCS), 2.52 (t,j=6.3Hz,4H 2N—CH$_2$CH$_2$—NH—CO), 1.51 (br s,12H,4CH$_3$—C—S) ppm. $^{13}$C NMR (in CDCl$_3$): δ 181.9 (s,N—CS—N), 175.2 (s,2NH—CO), 158.8 (s,3C$_1$—Ar—OCH$_3$), 130.0 (s,C$_1$—Ar—N), 130.0 (d,2C$_2$&C$_6$—Ar—OCH$_3$), 129.2 (s,2C$_4$—Ar—OCH$_3$), 127.0 (d,C$_2$&C$_6$—Ar—N), 114.5 (d,C$_3$&C$_5$—Ar—N), 114.2 (d,2C$_3$&C$_5$—Ar—OCH$_3$), 55.4 (q,3CH$_3$O), 54.4 (t,2N-CH $_2$CH$_2$—NHCO), 52.9 (t,N—CH$_2$CH$_2$—NHCS), 50.1 (s,2S—C—CH$_3$), 42.8 (t,N—CH$_2$CH$_2$—NHCS), 38.3 (t,2N—CH$_2$CH$_2$—NHCO), 34.2 (t,2S—CH$_2$—Ar), 28.3 (q,4CH$_3$—C—S) ppm. MS (m/z,FAB): 756(4.2, M$^+$). IR (CDCl$_3$): 3320, 2960, 1720, 1655, 1510, 1290, 1245, 1030 cm$^{-1}$.

Part 4: Labeling of an N$_3$S$_2$ Chelate

Synthesis of acyclic dimercapto-N,N,N-tris(2-aminoethyl)amine

Preparation of N,N-dimethyl-2-(3,3,5,11,13,13-hexamethyl- 1,2-dithia-5,8,11-triaza-cyclotridecan- 8-yl) ethylamine (27)[6]

To 2-(3,3,13,13-tetramethyl-1,2-dithia-5,8,11-triazacyclotridecan- 8-yl) ethylamine 4 (202.6 mg, 0.63 mmol), in a 25 mL round bottom flask, concentrated formic acid (4 mL) and 37% formaldehyde solution (3.7 mL) was added. The mixture was heated under reflux and stirred for 25 hours. The solution was then cooled to room temperature and extracted three times with ether (50 mL). The aqueous phase was rendered basic (≦10–11 ) by adding 27% ammonium hydroxide and extracted with methylene chloride (4×50 mL). The organic phase was washed successively with. water (50 mL) and saturated sodium chloride solution (2×50 mL), dried with anhydrous magnesium sulfate, and filtered. The solvent was removed under vacuum to give 176 mg (74%) of tetramethylated tetramine disulfide 27 as a yellow oil. The crude product was purified by flash chromatography (silica gel) using a mixture of methylene chloride, methanol, and ammonium hydroxide (84.5/15/0.5) as eluent. Pure N,N-dimethyl- 2-(3,3,5,11,13,13-hexamethyl-1,2-dithia-5, 8,11-triazacyclotridecan- 8-yl) ethylamine 27 (108 mg) was recovered from the purification process.

N,N-dimethyl-2-(3,3,5,11,13,13-hexamethyl-1,2-dithia-5,8,11-triazacyclotridecan-8-yl) ethylamine 27

$^1$H NMR (300 MHz,in CDCl$_3$): δ2.71 (t,J=6 Hz,4H,—N—CH$_2$-CH $_2$—N(CH$_3$)—), 2.64 (s,4H,—N—CH$_2$—C(CH$_3$)2—S—), 2.62 (t,J=6 Hz,4H,—N—CH$_2$—CH$_2$—N(CH$_3$)—), 2.52 (m,2H,—CH$_2$—CH$_2$—N(CH$_3$)$_2$), 2.46 (m,2H,—CH$_2$—CH$_2$—N(CH$_3$)2), 2.37 (s,6H,—CH$_2$N(CH$_3$)—CH$_2$—), 2.25 (s,6H,—CH$_2$—CH$_2$—N(CH$_3$)$_2$) and 1.28 (s,12H,—S—C(CH$_3$)$_2$—) ppm. $^{13}$C NMR (75 MHz,in CDCl$_3$): δ74.8, 67.7, 57.6, 57.2, 53.9, 51.7, 51.3, 45.9, 45.1 and 26.9 ppm. MS (El; m/z): 376(4, M$^+$), 377(2,M$^+$+1), 378(0.6,M$^+$+2), 318(1,M$^+$—((CH$_3$)$_2$N—CH$_2$')), 262 (3), 255 (1), 246 (1), 187(7), 156(9), 144(8), 133(9), 130(16), 113 (17), 101 (27), 99(21), 98(12), 72(32), 71(28), 70(42), 58(100), 56(13), 55(13), 43(31), and 42(38).

Reduction of N,N-dimethyl-2-(3,3,5,11,13,13-hexamethyl-1,2-dithiyl-1,2-dithia-5.8.11-triaza-cyclotridecan-8-yl) ethylamine (2.7)[6]

In a 50 mL three-necked flask equipped with a gas inlet device, a magnetic stirring bar, a stopper and a dry ice condenser 18.9 mg (0.5 μmol) of the tetramethylated tetraamine disulfide (27) was introduced. The condenser was filled with acetone and dry ice, and the contents of the flask was cooled with a dry ice bath. Liquid ammonia was then introduced in the flask until about 25 mL was added. The solution was stirred for several minutes and 36 mg( 1.6 mmol) of sodium was added. The mixture was stirred for thirty minutes, and ammonium chloride (172 mg) was cautiously added. The cooling bath was then removed to allow the ammonia to evaporate. The white residue was dissolved with 45 mL of Milli-Q water and concentrated hydrochloric acid was added to brougth the pH of this solution to 1. The mixture was extracted with ether (3×50 mL) and the pH was raised to about 9 with 37% ammonium hydroxide. The basic solution was extracted four times with ether (50 mL). The organic phases were combined, washed successively with water (1×30 mL) and brine (2×30 mL). The ethereal phase was dried with anhydrous magnesium sulfate and filtered. The solvent was then removed under reduced pressure to yield 16 mg of a yellow oil. This oil was used as it is to perform the Tc-m99-technetium labeling study.

Note: The HPLC analysis of this oil has shown that it is a mixture of two component in a ratio of 2.5/1: the starting material and the reduced compound. The HPLC conditions used for analysis were as followed: column Hamilton PRP-I 10 μm analytical, gradient of 10 to 50% of acetonitrile (with 0.1% TFA) in 40 minutes. Retention times: tetramethyl tetraamine disulfide≦ 7.73 min; tetramethyl tetraamine dithiol≦ 21.55 min. Tc-m99-technetium labeling of a mixture obtained from the reduction of N,N-dimethyl-2-(3,3,5, 11,13,13-hexamethyl-1,2-dithia-5,8,11-triaza-cyclotridecan- 8-yl) ethylamine Experiment A:

In a 1.5 mL plastic conical vial 30 μL of a methanolic solution (~2μg/μL) of the mixture obtained from the reduction of N,N-dimethyl- 2-(3,3,5,11,13,13-hexamethyl-1,2-dithia-5,8,11-triazacyclotridecan- 8-yl) ethylamine, 0.1 mL Tc-m99-technetium glucoheptonate (prepared by the reconstitution of a vial from a FROSSTIMAGE GLUCOHEPTONATE kit with 1 mL of sodium per$^{99m}$technetate) were introduced. This solution was stirred for 20 seconds with a vortex mixer and heated at 63° C. for 2½ hours. The mixture was then analyzed by ITLC@ (Instant Thin Layer Chromatography) ran in acetone and in normal saline and demonstrated that 90% of the radioactivity was tagged with the chelate. HPLC analysis* of the labeling mixture showed the presence of three radioactive products. The first radioactive compound was identified as $^{99m}$ technetium glucoheptonate ($R_T$:2.59 min; 19%) while the two others are $^{99m}$ Tc-$N_3S_2$ chelated species ($R_T$:20.72 and 23.08 min; 68 and 8% respectively).

Experiment B:

In a 1.5 mL plastic conical vial 30 μL of a methanolic solution (~2 μg/μL) of the mixture obtained from the reduction of N,N-dimethyl- 2-(3,3,5,11,13,13-hexamethyl-1,2-dithia-5,8,11-triazacyclotridecan- 8-yl) ethylamine, 0.2 mL $^{99m}$ technetium glucoheptonate (prepared by the reconstitution of a vial from a FROSSTIMAGE GLUCOHEPTONATE kit with 1 mL of Tc-m99-sodium per technelate) were introduced. This solution was stirred for 20 seconds with a vortex mixer and heated at 65° C. for 1 hour. The mixture was then analyzed by ITLC¶ (Instant Thin Layer Chromatography) ran in acetone and in normal saline and demonstrated that 85% of the radioactivity was tagged with the chelate. HPLC analysis§ of the labeling mixture showed the presence of three radioactive products. The first radioactive compound was identified as Tc-m99technetium glucoheptonate ($R_T$:2.72 min; 30%) while the two others are $^{99m}$Tc-$N_3S_2$ chelated species ($R_T$:20.70 and 23.08 min; 56 and 8% respectively).

¶: Gelman SG chromatography paper.

*: The high performance liquid chromatography analysis was performed with a Waters 625LC instrument equipped with a Hamilton PRP-I 10 μm analytical column using a 10 to 50% acetonitrile (+TFA) gradient in 40 minutes and a flow rate of 1 mL/min.

1. W. C. Still, M. Kahn, and A. Mitra, J. Org. Chem., 43, 2923–2925 (1978).

a) J. J. D'Amico and W. E. Dahl, J. Org. Chem., 40, 1224–1227

(1975) b) K. Masao, T. Ueno, K. Kojima and Y. Morimoto, (Nippon Shokubai Kagaku Kogyo Co., Ltd.) *Jpn. Kokai Tokkyo Koho* JP 63,222,155 [88,222,155].

3. E. A. Bayer, B. Haya and M. Wilchek, *Biochem. and Biophys. Res. Commun.*, 138, 872–879 (1986).

4. M. R. A. Pillai, J. M. Lo, C. S. John and D. E. Troutner, *Nucl. Med. Biol.*, 19, 791 (1992).

5. Y. Ohmomo, L. Francesconi, M. P. Kung and H. F. Kung, *J. Med. Chem.*, 35, 157 (1992).

6. M. Apparu, S. Drouillard, J. P. Mathieu, A. DuMoulinet D'Hardemare, R. Pasqualini, and M. Vidal, *Appl. Radiat. Isot.*, 43 (5), 585–596 (1992).

What is claimed is:

1. A compound of the formula:

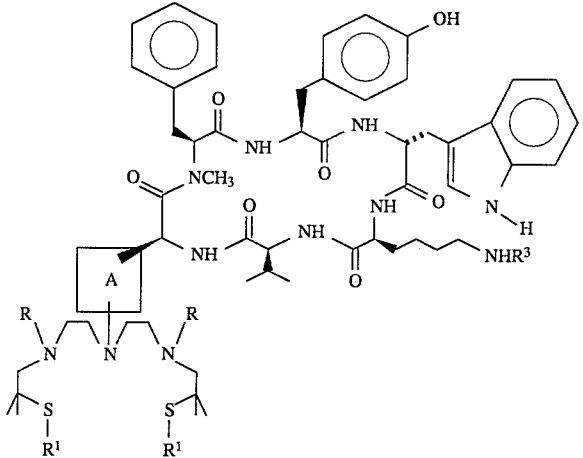

wherein:

R is selected from the group consisting of:

hydrogen
loweralkyl of 1–4 carbon atoms, and
loweralkyl carboxyl, wherein loweralkyl is 1–4 carbon atoms;

$R^1$ is selected from the group consisting of:
hydrogen, a sulfur protecting group, or $R^1$ and $R^1$ are linked together to form a bond between the two "S" groups;

m and n are independently an integer from 1–4;

$R^3$ is hydrogen or a blocking group selected from:
t-butoxycarbonyl (t-boc),
fluorenylmethoxycarbonyl (Fmoc), and
isonicotinyloxycarbonyl(i-Noc); and the linker

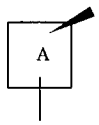

is selected from the group consisting of:

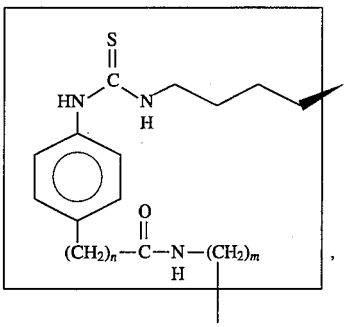

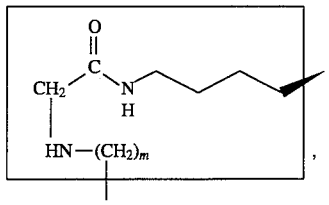

and

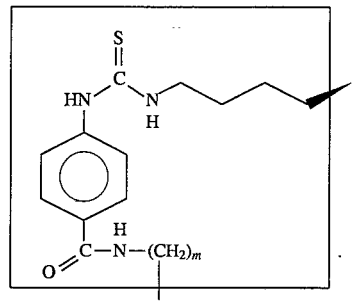

2. The compound of claim 1 wherein the definition of $R^1$ the sulfur protecting group is selected from the group consisting of:
p-loweralkyloxyl (1–4 carbon atoms) benzyl,
p-methoxylbenzyl, and trityl.

3. The compound of claim 1 wherein the linker

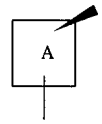

is:

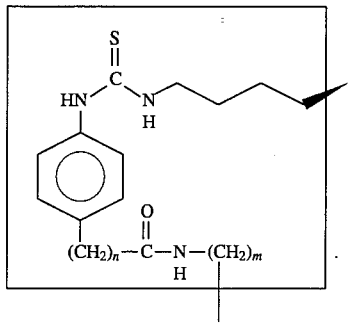

4. The compound of claim 1 wherein $R^3$ is hydrogen.

5. The compound of claim 3 which is chelated to Tc-m99 or Re-186.

6. A compound of the formula:

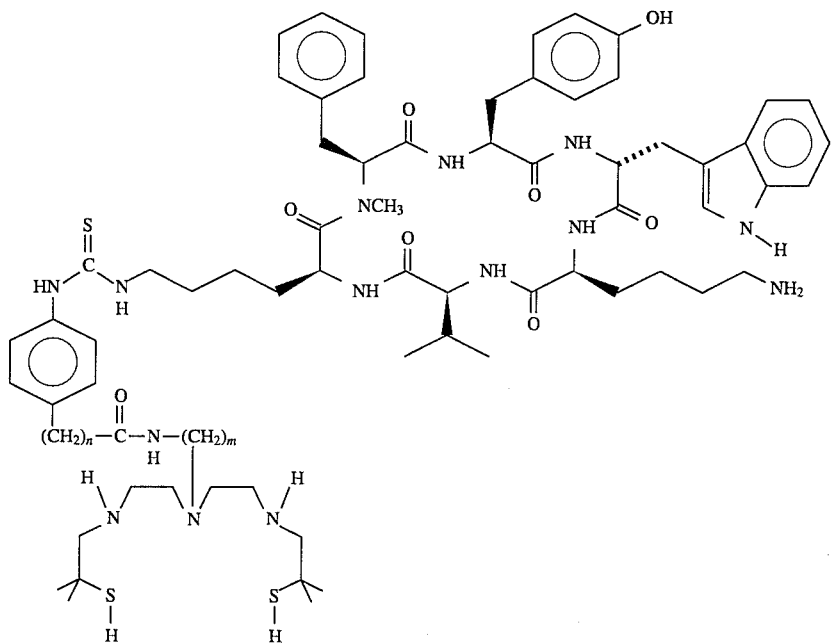
wherein m and n are independently an integer from 1–4.
7. The compound of claim 6 which is chelated to Tc-m99 or Re-186.
* * * * *